(12) United States Patent
Watson et al.

(10) Patent No.: US 6,177,994 B1
(45) Date of Patent: Jan. 23, 2001

(54) RELATING TO THE MEASUREMENT OF PARTICLE SIZE DISTRIBUTION

(75) Inventors: David John Watson, Hanley Swan; Clive Patrick Ashley Catterall, Malvern Wells; Duncan Edward Stephenson, Worcester, all of (GB)

(73) Assignee: Malvern Instruments Limited, Worcesterchire (GB)

( * ) Notice: Under 35 U.S.C. 154(b), the term of this patent shall be extended for 0 days.

(21) Appl. No.: 09/378,338

(22) Filed: Aug. 20, 1999

(30) Foreign Application Priority Data

Aug. 22, 1998 (GB) .................................................. 9818351

(51) Int. Cl.⁷ .................................................. G01N 21/00
(52) U.S. Cl. .......................... 356/343; 356/337; 356/339; 356/342
(58) Field of Search ..................................... 356/336, 337, 356/338, 339, 342, 343, 340, 341, 335; 250/574, 575

(56) References Cited

U.S. PATENT DOCUMENTS 5,260,764 * 11/1993 Fukuda et al. ........................ 356/366
5,416,580   5/1995 Trainer ................................. 356/336
5,576,697 * 11/1996 Nagashima et al. .................. 250/574

FOREIGN PATENT DOCUMENTS 0485817   5/1992 (EP) .
0559529   9/1993 (EP) .
1304962   1/1973 (GB) .

* cited by examiner

*Primary Examiner*—Frank G. Font
*Assistant Examiner*—Sang H. Nguyen
(74) *Attorney, Agent, or Firm*—John P. White; Cooper & Dunham LLP

(57) ABSTRACT

A particle size distribution analysis apparatus wherein there are provided a sample measurement zone adapted to contain a sample of particles, a light emitting means adapted to provide a source of light incident upon the measurement zone, and a detection means adapted to measure light levels at different scattering angles and to output signals to a computation means, enabling the size of particles contained within the sample to be determined, wherein the light emitting means comprises a first light source emitting a substantially monochromatic first wavelength of light and a second light source emitting a substantially monochromatic second, different, wavelength of light.

24 Claims, 4 Drawing Sheets

RELATING TO THE MEASUREMENT OF PARTICLE SIZE DISTRIBUTION

Figure 1:
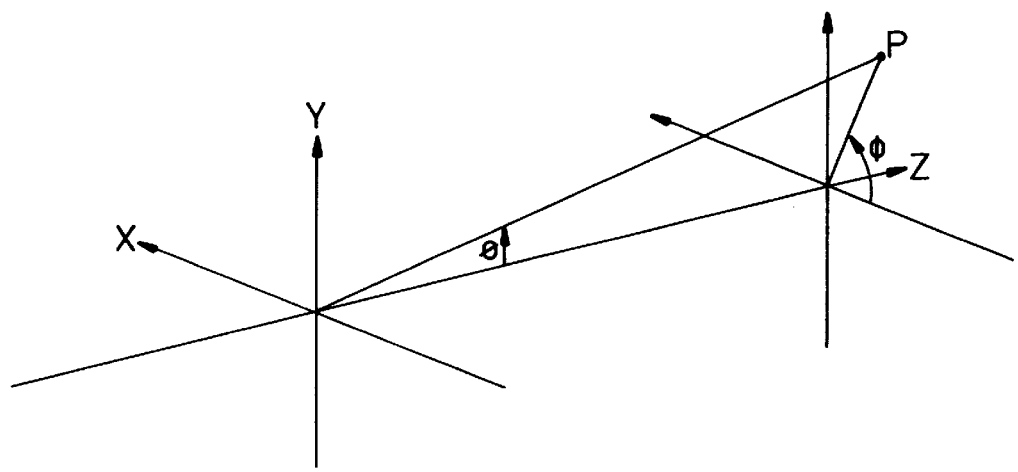

This invention relates to an improved apparatus and method for measuring particle size distribution, It is known to provide particle size distribution analysis apparatus which rely on the scattering of light incident upon a sample of particles and have multiple laser sources at different angles relative to a cell containing the sample. An example of such a system is shown in EP 0 559 529 wherein a further beam of laser produced light is introduced by an optical fibre at an angle to the main laser beam. In such systems the minimum size of particle which can be detected is reduced by transforming the information from the extra, angled, lasers in to further angular information. It is also known to introduce an extra light source and filter to achieve further information as shown in U.S. Pat. No. 5,164,787.

It will be appreciated that the term particle may mean any phase of a discontinuous material contained within a continuous phase of a supporting medium. Either phase may be gaseous, liquid or solid. The only physical limitation is that the particle must have a different refractive index to the medium and further, that the medium must be substantially transparent at any illuminating wavelength of light.

According to a first aspect of the invention there is provided a particle size distribution analysis apparatus wherein there are provided a sample measurement zone adapted to define a sample of particles, a light emitting means adapted to provide a source of light incident upon the measurement zone, and a detection means adapted to measure light levels at different scattering angles and to output signals to a computation means, enabling the size of particles contained win the sample to be determined, wherein the light emitting means comprises a first light source emitting a substantially monochromatic first wavelength of light and a second light source emitting a substantially monochromatic second, different, wavelength of light.

An advantage of such a system is that the range of particle sizes which can be determined by the calculation means is increased over a system with only a single light source.

In the preferred embodiment at least the first source is a laser, possibly a He/Ne laser and preferably a red light laser.

Preferably at least the second light source is an LED (light emitting diode). This has the advantage that a cheap and robust light source is. provided which has a longer life than other light sources, is physically small, and does not produce a large amount of heat.

In another embodiment at least the second light source may be a laser diode.

Some prior art systems have provided a plurality of light sources. However, such prior an systems have tended to use a second source which was not mono-chromatic, for example a tungsten halogen source. The provision of such a light source is disadvantageous because it is bulky, does not have a long life, produces a large amount of heat, must be left energised for long periods to ensure thermal equilibrium is achieved and for application to the arrangement of the present intention would require filtering means to ensure that only a substantially monochromatic light were output.

The second light source may output light with a wavelength substantially in the range 350 nm to 550 nm. The second light source may output light with a wavelength substantially in the range 400 nm to 500 nm and possibly the second light source may output light with a wavelength of substantially 466 nm. The skilled person will appreciate that in the preferred embodiment the second light source should output light with as small a wavelength as possible but that practical considerations may mean that a compromise wavelength is used. Such considerations include cost of manufacture, availability of suitable light sources, the stability of available sources, etc.

The second light source may emit light that is monochromatic enough so that it does not need filtering to achieve analysable scattering results (i.e. no monochromatic filter may be provided). Alternatively, for some applications we may provide a filter.

The first light source may output light with a wavelength substantially in the range 533 nm to 2 $\mu$n. The first light source may output light with a wavelength substantially in the range 583 nm to 683 nm and in one embodiment the first light source may output light with a wavelength of substantially 633 nm. The skilled person will appreciate that the choice of wavelength of the first light source may be influenced by practical considerations.

The light sources may emit light with wavelengths differing by substantially 170 nm or may be by substantially 300 nm, 250 nm, 200 nm, 150 nm, 100 nm or 50 nm. However, the skilled person will appreciate that the it is desirable to have a larger wavelength difference than this and also that the device may well work with a wavelength difference smaller than this.

Preferably the light sources are arranged so that beams of light emitted substantially superpose (or substantially superimpose) one another on the measurement zone. This has the advantage that the structure of the apparatus is simplified.

The second light source may be arranged so that a beam of light that it emits is inclined at an angle to a beam of light emitted from the first light source. Again, this has the advantage that the structure of the apparatus is simplified. The second light source may be arranged at an angle substantially in the range 0° to 30° to the beam of light emitted from the first light source. The second light source may be arranged at an angle substantially in the range 10° to 20°. In the most preferred embodiment the second light source may be arranged at substantially 10° to 15°, most preferably at 15°±1°.

It is advantageous to allow the second light source to pass directly through the sample by inclining the beam at an angle to the beam emitted from the first light source as this means that no beam splitter is required, thus simplifying the optical components of the system.

Preferably light emitted from the second light source and the optical axis of the first light source lie in a plane which is inclined at an angle $\phi$ to a plane in which the detection means (which may include a large angle detector, a forward angle detector, a focal plane detector, s back scatter detector) is situated. Preferably the angle $\phi$ is substantially a right angle. For the avoidance of doubt this is illustrated in FIG. 1 of the accompanying drawings wherein the optical axis of the first light source is along the z axis, light emitted from the second light source is inclined at angle $\phi$ to the z axis in the yz plane and wherein the detection means is provided in the xz plane.

The second light source may be adapted, in use, to be pulsed. This has the advantage that the signal to noise ratio of the system may be increased and also the peak intensity of the system may be increased.

At least one light output stabilisation means may be provided to ensure that the light emitted from either (or both) of the light sources is constant. Preferably a first light source stabilisation means is provided to monitor the first light source and/or an a second light source stabilisation means is provided to monitor the second light source.

The stabilisation means may comprise a primary monitoring means and primary processing means. The processing means may be connected in a closed loop which uses the detected signal from the primary monitoring means to control the output power of the light emitted from the respective light source. Alternatively, or additionally, instead of controlling the output of the light source to be stable we may allow it to fluctuate and the primary processing means may output a signal representative of the light power emitted from the respective light source to enable provision for fluctuations in the light power emitted from the light source in subsequent calculations relating to the particle sizes.

One of tie light sources may have the processing means connected to a closed loop in order to control the output power of the light source and the power from the other of the light sources is allowed for in subsequent calculations relating to the particle sizes. Preferably it is the second light source which is monitored with a closed loop monitor and has its output power so controlled. Further, it is preferable for the laser to be monitored and the signal representative of the of the light power emitted from the light source to be allowed for in subsequent calculations relating to the particle sizes.

The stabilisation means may further comprise temperature, stabilisation means providing provision to take into account the variation in temperature of the apparatus. The temperature stabilisation means may comprise a monitoring means and processing means, which may be substantially identical to the primary monitoring and primary processing means, and the primary processing means may be arranged so that no light is received by the monitoring means. Temperature variation compensation may be provided only for one light source (e.g. the second light source), or for both. We may prefer to arrange for the first light source to be left on substantially continuously during an operational programme, with the second light source being turned on and off periodically, which will minimise temperature changes for the first light source.

The detection means may comprise a plurality of detectors arranged substantially in a plane. The second light source and beam emitted from the second light source may be provided in a plane transverse to the plane of the detectors of the detection means. Preferably, the plane of the second light source and beam emitted from the second light source may be substantially perpendicular to the plane of the detectors of the detection means.

Preferably the beam of light output from the first light source is collimated. Collimation may be achieved by the use of lenses.

A second light source transmission detector may be provided to measure the level of light from the second light source transmitted through the measurement zone. Preferably the second light source transmission detector is situated substantially directly opposite the measurement zone from the second light source (along a straight line).

A first light source transmission detector may be provided to measure the level of light from the first light source tramsmitted through the measurement zone. Preferably the first light source transnmission detector is situated substantially directly opposite the measurement zone from the first light source.

The detection means may comprise one or more of the following in addition to the second light source and the first light source transmission detectors: a large angle detector adapted to detect light reflected at large angles by the sample, a bat scatter detector adapted to detected light reflected back towards the light source by the sample, forward angle detectors adapted to detect light reflected at medium angles by the sample and a focal plane detector adapted to detect light reflected at small angles by the sample.

The large angle detectors may detect light reflected from a light source by the sample at angles substantially in the range of 80° to 30° from the axis of the laser beam with the direction of travel of the incident laser light taken as 0°. There may be two large age detectors possibly situated substantially at 45° and 60°.

The back scatter detectors may detect light reflected from a light source by the sample at angles substantially in the range of 100° and 150° from the axis of the laser beam with the direction of travel of the incident laser light taken as 0°. There may be two back scatter detectors possibly situated substantially at 120° and 135°.

The forward angle detector may be situated substantially in the range of 15° to 45° from the axis of the laser beam with the direction of travel of the incident laser light taken as 0°. The forward angle detector may comprise an array of detectors and may in the preferred embodiment comprise nine detectors in an array.

The focal plane detector may be situated substantially in the range of 0° to 30° from the axis of the laser beam with the direction of travel of the incident laser light taken as 0°. The focal plane detector may comprise an array of detectors and in the preferred embodiment comprises an array of thirty three detectors.

Preferably the large angle detectors and the back scatter detectors receive light from both of the light sources. Conversely the second light source and first light source transmission detectors may be designed to received light only from the second light source and first light source respectively. The readings from the focal plane and forward angle detectors may only be valid for scattering of light from the laser.

A computational element (e.g. a computer or microprocessor) may be adapted to determine the obscuration of the light emitted from the second light source. The computational element may also be adapted to determine the obscuration of the light emitted from the first light source.

The large angle detectors may be provided at substantially a first angle relative to the measurement zone and the back scatter detectors may be provided at 180° minus the first angle relative to the measurement zone.

That is the back scatter detector may be provided as a mirror image of the large angle detectors.

According to a second aspect of the invention there is provided a method of determining particle size distribution comprising illuminating a sample of particles with first and second beams of light, emitted from first and second light sources respectively, the beams having different wavelengths and being substantially monochromatic and the method further comprising measuring light levels around the sample to determine the particle size distribution within the sample.

Preferably the first light source is an LED and most preferably a blue LED. The second light source may be a laser.

The method may comprise illuminating the sample with light from each source sequentially and may comprise using substantially the same detection means to measure light levels produces by each light source.

The obscuration of the light emitted by the first light source and passing through the sample may be calculated giving a first light source obscuration signal. Further, the obscuration of the light emitted by the second light source passing through the sample may be calculated giving a second light source obscuration signal. The first light source and the second light source obscuration signals may be used in conjunction to increase the range of particle sizes measured by the method.

The method may comprise using the light level measurements taken using light from each detector and manipulating them so that the measurements comprise a single data set as if the measurements had been taken by a single wavelength of light.

Detecting forward angle scattering signals may be used to compensate detected back scattering signals for reflections of forward scattering, thereby producing a processed back scattering signal that is not the same as the detected back scattering signal.

The detected forward angle signal may be subtracted from the detected back scattering signal to produce the modified, processed, back scattering signal.

Figure 2:
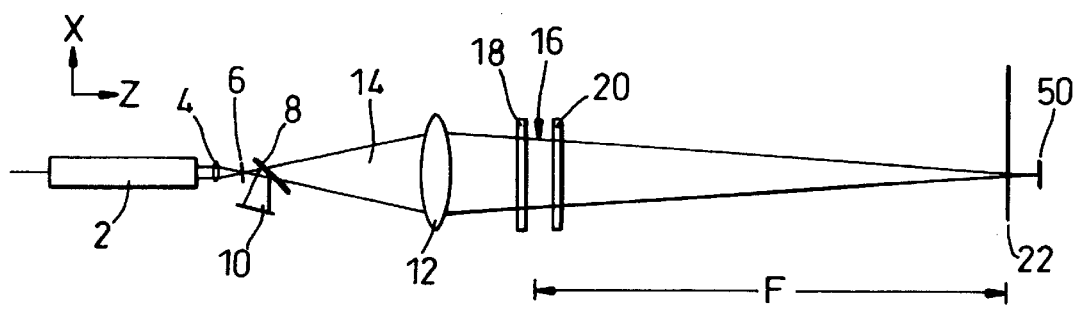
Figure 3:
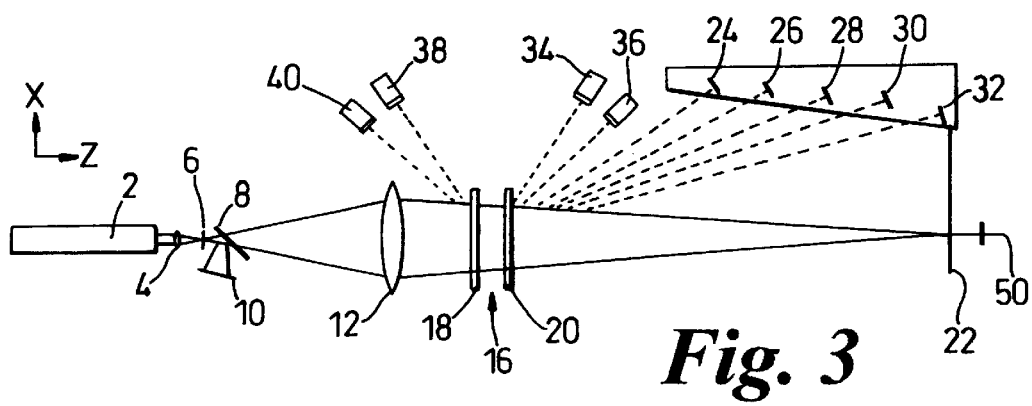
Figure 4:
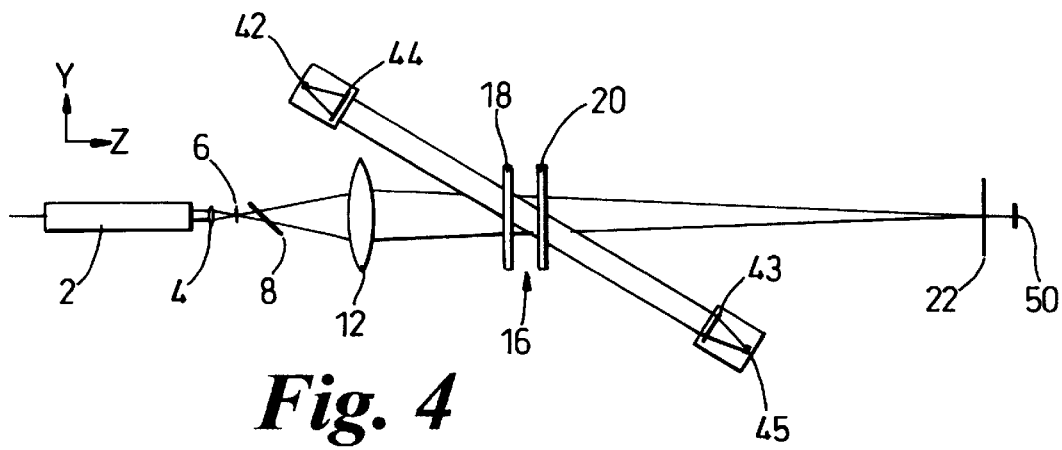
Figure 7:
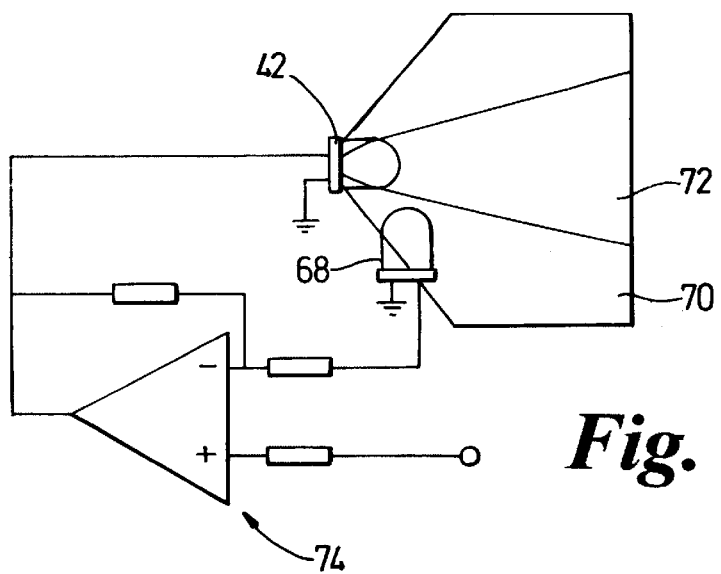
Figure 6:
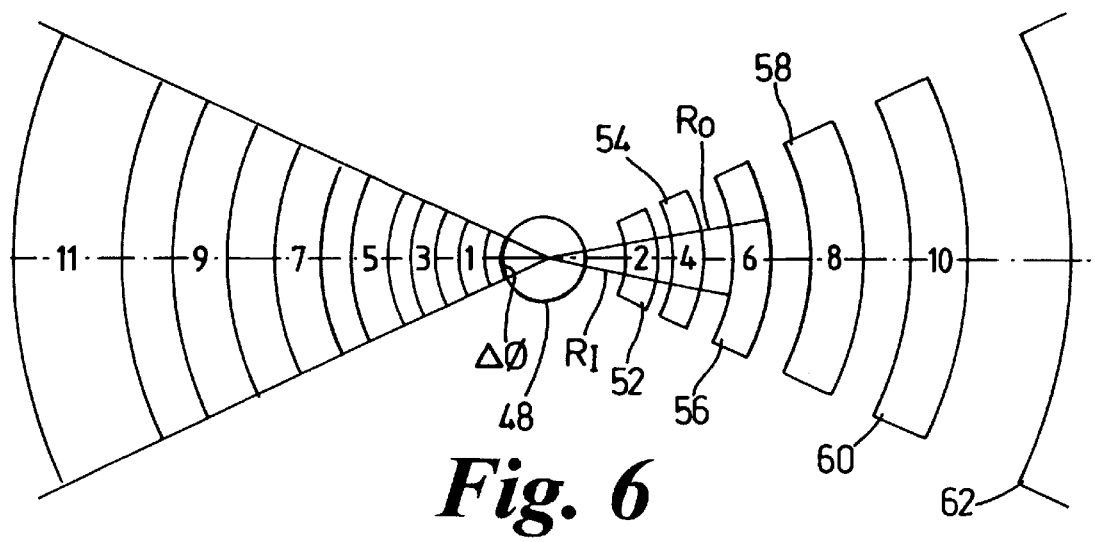
Figure 5:
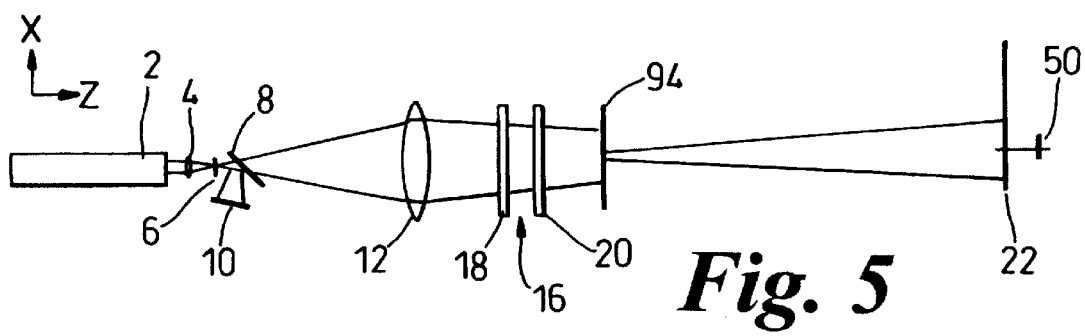
Figure 9:
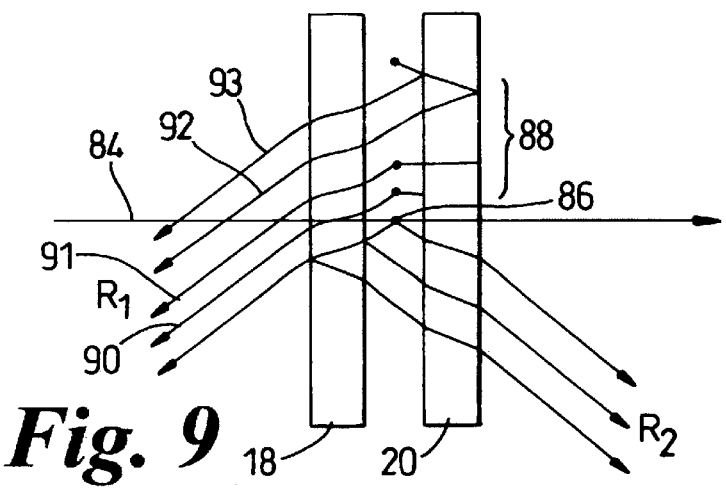
Figure 8:
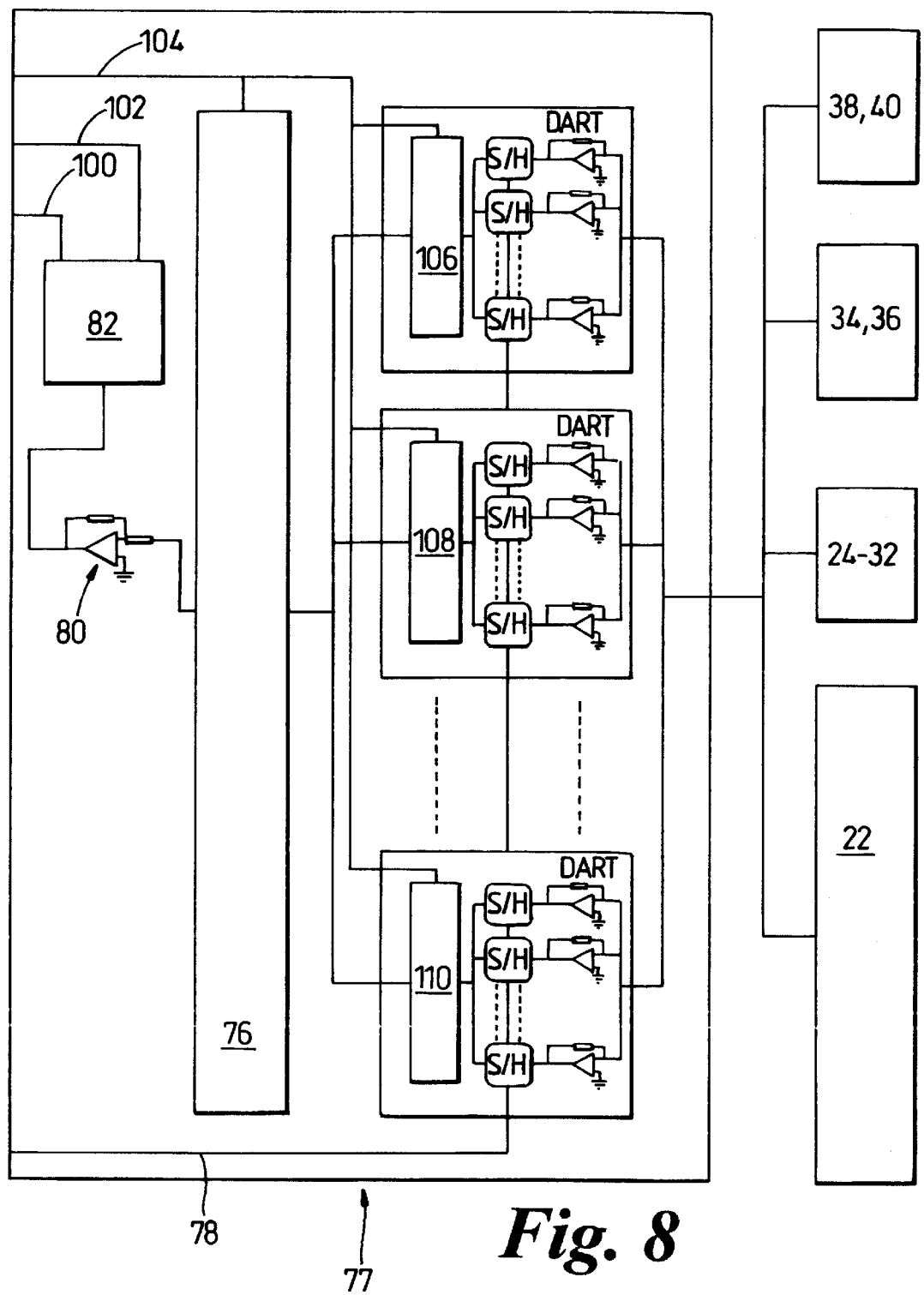

There now follows by ways of example only a detailed description of an embodiment of the invention with reference to the accompanying drawings of which:

FIG. 1 shows the co-ordinate system used;
FIG. 2 shows a basic system configuration;
FIG. 3 shows an enhanced system configuration;
FIG. 4 shows a further enhancement of the system shown in FIG. 3;
FIG. 5 shows an optical arrangement allowing the system to be calibrated;
FIG. 6 shows an arrangement of detectors;
FIG. 7 shows a schematic circuit for stabilising a light source of FIG. 4;
FIG. 8 shows a schematic of the signal and collection circuits of the system; and
FIG. 9 shows the reflections occurring from a sample cell of the system.

FIG. 2 shows a schematic of a basic particle size distribution measuring apparatus wherein a low power laser source 2 (light emitting means), typically a He—Ne laser is beam expanded and spatially filtered to produce a larger collimated beam containing only the TEM 00 mode of laser propagation. A lens 4 and a spatial filter component 6 positioned in the focal plane of the lens 4 achieves this.

A beam splitter 8 is typically used in order to allow a small fraction of the laser power to be directed onto a laser monitor detector 10. This detector 10 allows the incident laser power to be monitored and any fluctuations corrected. It is important in the sub-micron measurement of particles to ensure that the laser power does not fluctuate between the sample and background measurement stages. For this reason optical sources are always either directly stabilised or monitored so that compensation can be performed. Non laser and semiconductor laser optical sources can be readily power controlled, however gas lasers need to operate in a steady state mode.

Although intensity control of a gas laser can be achieved by feeding the detector signal into the measurement electronics as gain compensation (for example it can be used to modulate the ADC reference voltage so that the ADC conversion characteristic is constant regardless of laser power) it is preferred to use a different and better approach. The laser power is read as a data value and allowed for by performing a scale correction during subsequent data processing by a signal processing unit.

A moveable shutter (not shown) is provided to turn off the laser and can be introduced under system control allowing the laser illumination to be blocked from impinging on a sample cell without in fact removimg power from the laser. This is a commonly employed approach for gas lasers, which do not respond well if turned off and on frequently. The purpose of the shutter is to allow the laser power to be removed in certain measurements of the detection system, for example, dark current and electronic offsets (and when using a second light source to scatter from the sample).

A range lens 12 then focuses the beam 14 so that a diffraction limited spot is produced in a plane of a focal plane detector 22. The laser beam also passes through a sample region 16 (or measurement zone) into which sample particles will be introduced.

In principle the sample region or measurement zone needs no physical parts to define it, since particles may be driven through the beam without any form of containment. However, it is preferred to provide a "sample cell" (acting as a sample continent means, or measurement zone) in order to provide protection of the optical system and containment of any particle carrier fluids. A sample cell would typically consist of two glass windows 18, 20 spaced apart by a well defined distance which are built into a cell body (not shown) designed to contain and suspend/circulate the particles in a carrier medium.

The windows 18, 20 allow the access and egress of the laser beam and of scattered light from the sample particles over the required practical range of the system. The carrier medium may be liquid or gas, the most common media being water and air. The sample region or cell 16 is the intersection of the laser beam diameter with the space between the containment windows 18, 20.

The sample region 16 is positioned at a known distance F from the focus point of the laser beam. The dimension F is critical in that it defines, for a given set of components, the available size range of the system for the system shown in FIG. 2. If further detectors are added the particle size distribution which can be measured is extended.

At the focal point of the laser beam a multi-element focal plane detector 22 is positioned, conventionally constructed as a single silicon photodiode array and an example of such a multi-element detector layout is shown in FIG. 6.

In the remaining description the following co-ordinate system has been used and is shown in FIG. 1. The direction of the first light source or laser light propagation is assumed to be the positive Z direction. The X-Z plane is assumed to be the "horizontal plane" and Y-Z the "vertical" plane. The arrows indicate the positive direction for all co-ordinates. Angle $\theta$ indicates the scattering angle away from the laser axis Z to an arbitrary-point P, in the plane containing both Z and P. The angle $\phi$ is the azimuthal angle from the X-Z plane around the Z axis to the point P.

Performance enhancing improvements to the basic system of FIG. 2, allowing smaller particles to be detected, are shown in FIGS. 3 and 4.

The skilled person will realise that in some prior art systems multiple laser sources at different cell entry angles are used allowing the detector to be transformed into apparently new collection angles. Also, some prior art system utilise multiple detection systems with a single laser source to achieve the same effect. Although not commonly employed any permutation of these principles is also possible.

In the preferred embodiment a further array of detectors is used to extend the optics described earlier as shown diagrammatically in FIG. 3. The extra detectors decrease the minimum size of particle which can be measured pushing the detectable particle size down to approximately 0.2 $\mu$m.

A series of nine forward angle detectors are provided although only five are shown in the FIGS. 24, 26, 28, 30, 32 on a PCB that runs the length of a cell-detector void. The detectors 24, 26, 28, 30, 32 are mounted physically aligned to face the cell 16. Each detector 24, 26, 28, 30, 32 is located at a special distance and angle from the cell 16 which is selected to optimise the information content of the entire system.

As the position of a detector depars from the focal plane of the lens 12 the detector no longer perfectly integrates over θ. Instead the detector measures signals over an additional Δθ which increases the nearer the detector is to the cell 16. This error in the angular collection of the detector can be predicted and therefore taken account of in a theoretical model of the system. In addition it is known that the light scattering characteristic changes more slowly as the angles become larger and thus the effect of the slight integration error becomes smaller and eventually negligible. The detectors 24, 26, 28, 30, 32 are provided and can be considered to be a simple angular continuation of the signal received on the focal plane detector 22. Indeed in the preferred embodiment the detectors 24, 26, 28, 30, 32 are routed into the same signal conversion electronics as the signals from the focal plane detector 22, Because of the reducing angular dependence of the signal it is normal for the detectors 24, 26, 28, 30, 32 not to form a continuous angular sequence since no information can get "lost" in the gaps. Further, the detectors 24, 26, 28, 30, 32 are rectangular or circular standard components and not the angular ring structure of the focal plane detector 22.

At angles approaching 45° or greater a new problem in signal detection becomes relevant. The detectors 24, 26, 28, 30, 32 are operating as simple line of sight detectors and thus they see also the stray reflections from the cell 16 (and multiple reflections). At forward angles the scattering from particles is strongly dominant and the stray multiple reflections are safely ignored. At the larger angles the tilt of the cell brings the cell walls more directly into view and the particle scattering intensity is typically masked. That is the detector field of view eventually brings the cell wall into view and the detector consequently collects light reflected from the cell wall as well as light scattered by the particles. This forces consideration of the proper spatial filtering of the received detector signals at larger angles.

As a consequence for these larger angles (that is angle approaching 45° or greater) a detector is produced as a small element positioned in the focal plane of a collection lens. The combination forms a spatial filter, and ensures that the detector receives light only from a narrow collection angle. This allows the cell wall signals to be acceptably rejected and not interfere with the measurement. Because of this additional complexity these detectors are used sparingly and referred to as large angle detectors 34, 36 in FIG. 3.

A further enhancement of the basic system of FIG. 2 is also shown in FIG. 3 and comprises providing back scattering detectors 38, 40. These detect light scattered by particles from the rear of the cell; that is where 90°<θ<180°. This detection is particularly important for the submicron determination of particle size. However light scattered at backward angles has poor angular variation and thus there is little need to sample at small angular increments. The back scatter detectors 38, 40 have mirror symmetry with the large angle detectors 34, 36 about an X-Y plane passing through the sample cell, and are constructed in an identical manner. The mirror symmetry is a convenience that allows for a simple correction of the large angle 34, 36 and back scatter 38, 40 detectors for the high cell reflectivity that occurs at these large exit angles from the cell 16.

Thus the basic approach of the preferred embodiment has a detection means comprising a focal plane detector 22 of thirty three elements, a transmission detector 50, an forward angle array of nine further elements, two large angle detectors 34, 36 and two back scatter 38, 40 detectors. The detectors are all disposed in a single plane with respect to the laser polarisation plane.

FIG. 4 shows a schematic of a further enhancement of the system shown and described in relation to FIG. 2 which allows the system to measure particles to a size of less than 0.1 μm and to improve the resolution for particle sizes of less than 1 μm.

A second light source with a shorter wavelength than the laser 2 is provided and the large angle and back-scatter responses to this light are measured to gain the extra resolution. The use of shorter wavelengths is the key to the bottom end size reduction and the combination of the two wavelengths increases the available sub-micron resolution of the system.

The shorter the wavelength the greater the enhancement to the sub-micron range and resolution. However there are practical considerations that prevent a substantial reduction in wavelength at effective cost. Thus only visible light wavelengths may be a practical option. In the system of FIG. 4 an LED 42 (a light emitting means) which emits blue light has been used. Other sources such as laser diodes may be used.

The sub-micron performance is only enhanced by the large angle scattering from the additional optical measurement and small angle scattering is largely redundant as it is duplicating data in the original measurement. Thus there is no need to produce a reduced wavelength light source 42 capable of the same stringent spatial filtering as the main optical system. This means that the requirements for collimation of the second beam are reduced significantly since only large angle scattering needs to be measured and the light output of an LED or laser diode is sufficiently collimated and monochromatic.

Further, the source 42 need only be near monochromatic rather than have the wavelength purity of the laser source 2. This is because small wavelength errors are equivalent to small angular errors. For the large angles of interest the angular dependence of particle scattering is reduced and thus the wavelength spreading effect becomes negligible.

Thus the blue LED 42 or laser diode emitting a blue beam of light are two examples of suitable sources provided they have a narrow spectrum of output light, typically ±50 nm. The ability to use an LED or laser diode as the source significantly reduces the cost of implementation and improves the long-term robustness.

The shorter wavelength second light source 42 is provided off-axis to the laser source 2 and in a plane perpendicular to the plane formed by the detectors 24, 26, 28, 30, 32 and the large angle 34, 36 and the back scatter 38, 40 detectors. (That is FIG. 4 has been rotated 90° about the z axis relative to FIG. 3). If the angle of the beam from the second light source 42 relative to the z axis is kept small it is possible to re-use the large angle 34, 36 and the back scatter 38, 40 detectors in measurements using both light emitted from the second light source 42 and the laser 2. This has the benefit of avoiding the cost of further detectors specifically for measurement of signals produced by the second light source 42. Although feasible it may not be considered necessary to utilise the larger angle elements of the detectors 24, 26, 28, 30, 32 for the short wavelength requirements (or we may re-use them in this way in other embodiments).

In the preferred embodiment the second light source 42 is provided at a shallow angle, typically 10–15° to the main beam path, sufficient to allow the optical components to co-reside without mechanical interference.

In one embodiment the second light source is an LED 42 and has a wavelength of typically 466 nm and with a narrow spectral range, typically +/−30 nm half width, half height. The light emitted from the LED 42 is collected and collimated by a single lens 44 which projects a beam through the cell windows 18, 20 at the same physical location as the beam from the laser 2. Thus the same cell 18, 20 windows are effective for measurements from both the LED 42 and the laser 2 and there is no need for a dual cell configuration.

The LED 42 projects the blue beam through the cell 16 so that it superposes the area where the beam from the laser 2 intercepts in the cell 16 (preferably exactly superposes). The unscattered beam from the LED 42 exits the cell 16 and is collected by an LED transmission detector 45 that measures the transmission of the blue beam through the cell. This LED transmission detector 45 also requires spatial filtering in order to improve the angular resolution of the measurement. This is achieved by use of a detection scheme (identical to that of the large angle 34, 36 and back scatter 38, 40 detectors described earlier), having a small detector element 45 in the focal plane of a collection lens 43.

The structure of the focal plane detector 22 is shown in FIG. 6. A centre of the focal plane detector 22 comprises a structure that is designed to allow the monitoring of the unscattered laser beam power. This may be implemented in one of three forms, a hole drilled through the wafer from which the detector is fabricated, a detector structure built on the wafer surface, or a mirror-like element that reflects the laser beam off the surface to an auxiliary detector mounted elsewhere. Each solution is aimed at allowing a measure of the power of the focused spot, which gives the power of the unscattered laser 2 output power.

In the preferred embodiment the wafer 46 from which the focal plane detector 22 is fabricated is drilled completely through from front to back with a small hole 48 of exact diameter and positioning. The focal plane detector 22 is aligned with the laser beam so that the diffraction limited spot falls down through the hole and out of the rear of the focal plane detector 22. A P.C.B (not show) supporting the wafer 46 is provided with suitable clearance holes to allow the beam to expand from the rear of the focal plane detector 22 and to fall onto a transmission detector 50.

In addition to the central hole 48 the focal plane detector comprises a series of annular ring detectors (51 to 62). Each detector is defined by an inner $R_I$ and an outer $R_O$ radial boundary, and an azimuthal angle $\Delta\phi$. The detectors may be constructed with a wide variation in the number of ring detectors provided and spacing in the spacing of each of the detectors, each different design trying to optimise the system. [For clarity, only twelve ring detectors are shown in FIG. 6, but there may be any other number. In one embodiment there are thirty three detectors.]

If the focal plane detector 22 has no hole and the transmission detector were provided on the surface of the focal plane detector 22 then it is possible to construct the transmission detector 50 as three or four sub-elements. The laser beam is then adjusted until it equalises the signal contribution from each sub-element, the sum of all elements being used as the reading. Whilst this is a convenient layout it suffers from specific disadvantages. The first is that it depends on the beam having circular symmetry, whereas the real beam may have aberration. The second is that the detector structures are very small and are thus subject to significant error in dimensions through photolithography limitations.

In another embodiment the focal plane detector 22 has a hole at a centre portion and an auxiliary transmission detector 50 to measure the initial laser beam intensity and it is possible to similarly split this detector into sub elements. Again the beam is adjusted to balance the relative powers on the sub-elements with the entire signal being used as the transmission measure or level of initial laser beam power. This approach eliminates the problem of having detector elements of small sizes since the beam has expanded considerably by the time it hits a transmission detector 50 beyond the focal plane detector 22 and typically expands to substantially 3 mm. Thus, the sub-detectors of the transmission detector 50 can be larger with the same discrimination.

However it adds new difficulties in that the transmission detector 50 is normally mounted to the focal plane detector 22 by hand and thus its alignment with the centre of the focal plane detector 22 has to be calibrated during assembly in some way. Given the extreme precision involved this requires extra expense. In addition since in some systems multiple ranges are achieved by changing the distance F, the alignment of the detector normal to the Z direction must be exact to avoid the alignment point apparently moving at different range positions.

A single detector element provides an integration (over time) of the light scattered by particles into those angles received between the $R_I$ and $R_O$ boundaries. These angles are also determined by the cell 16—focal plane detector 22 distance F (as shown in FIG. 2). It may be possible to arrange the lens 12 so that cell 16 to focal plane detector 22 length F is varied. Such a variable arrangement allows a wider range of angles to be covered by the instrument in a series of size ranges determined by the distance F. In the preferred embodiment a single range lens 12 and a fixed cell 16—focal plane detector 22 distance, F, with range extension being achieved by the use of the large angle 34, 36, the back 25 scatter 38, 40 and detectors 24, 26, 28, 30, 32.

In order to measure the largest possible particle sizes the inner detector 51 wants to measure the smallest angles possible and in practise means that the size of the central hole 48 needs to as small as is practical whilst collecting all of the beam from the laser 2 with the first detector as close to the boundary of the hole 48 as possible. The practical limits of photolithography and micromachining determine this smallest detector dimension.

In order to measure the smallest particle Sizes the detectors need to subtend larger angles, eventually even back-scatter angles are required. There is a clear practical limit to the range of angles that can be covered by a system having only a focal plane detector 22. The limit is determined by the largest physical dimensions that can be integrated into the planar focal plane detector array and such systems are typically limited to angles up to 30°, which prevents accurate sizing below 0.3 $\mu$m.

As discussed hereinbefore the light sources must be stabilised or corrections made for the power fluctuation. Unlike the laser 2 the LED 42 has desirable properties with regard to light power control in that it can be turned on and off at will and rapidly stabilises in output power. It can also be readily temperature stabilised, and outputs relatively little heat. The output power can therefore be controlled by modulation of the LED 42 current. For these reasons the power control of the LED is accomplished by a closed loop electronic control system shown in FIG. 7.

The LED 42 output power is monitored by a stabilisation means which comprises a photodiode monitor 68 (primary monitoring means). The monitor 68 requires no beam splitter or special optics since the LED 42 has sufficient optical losses that the detector can monitor using the stray light 70 lost from the LED plastic body. The stray light is represented in the Figure by the outer region around the main beam 72 from the LED 42. The monitor 68 provides a feedback signal to a current control circuit 74 (or primary processing means) that varies current to the LED 42 until an output power is achieved that matches an input control demand.

In order to provide temperature compensation for the LED stabilisation means a further identical detector held in blackout conditions but under the same temperature environment way be used to provide a temperature stabilsation means. This allows the monitor signal to be compared differentially with the signal from the blacked out detector giving common mode rejection of temperature variation.

This provides a stable known output light intensity from the LED 42 that is entirely electronically servo controlled. This implies that the LED 42 power monitor does not require that it be fed into the computing element (as is done with the reading from the laser monitor detector 10), since it can be taken as pre-calibrated.

An alternative/different approach to providing the same control effect would be to feed the signal from the monitor 68 into the computational element 77 so that the gain compensation could be performed by digitally re-scaling the data obtained using the LED 42. (That is as is done with the signal from the laser monitor detector 10). This would avoid the need for closed loop control of the LED 42 power supply, which could instead then work as a constant current source. We prefer to stabilise the LED since it is an elegant solution and avoids unnecessarily complicated computational calculations.

In order to enter the data into a computational element 77 it is fundamentally necessary to multiplex parallel data produced by the system to a serial stream that can be read through a common interface. There are many conventional ways to perform this using electronic systems, analogue, digital or bus based multiplexers an all commonly utilised singly or mixed.

In the preferred embodiment the arrangement in FIG. 8 is used to process the data produced by the system. Each detector in the system (the detectors are represented on the right hand side of the Figure and are connected via busses to the remaining circuitry of the Figure), is provided with its own dedicated transimpedance gain amplifier followed by a sample and hold stage (represented by S/H in the Figure). The gain stage of the amplifier lifts the signal levels to a sufficient level to allow the following signal processing to introduce negligible error.

The sample and hold circuits S/H are connected to a common timing line 78. An address line 104 is connected to the multiplexers 76, 106, 108, 110. The analogue to digital converter 82 is connected to a data line 102 and a timing lines 100.

The parallel outputs of the detectors (apart from the LED stabilization means) are fed to a multiplexing element 76 that is conventionally implemented as a cascade of analogue multiplexers. Equally the multiplexing is sometimes achieved digitally using control of output enables of bus connected drivers.

The single channel of output is further gain and offset adjusted by an amplifier 80 and then input to an Analogue to Digital Converter (ADC) 82. The ADC will, on command, convert the signal value to a digital representation at a specified level of precision. This value is then read by a computational device (not shown), typically a microprocessor and read into a memory location.

The computational element operates on the scattering data to fit it to known Fraunhofer and/or Mie Scattering theories to evaluate the particle size distribution by evaluating the best fit distribution that would produce the detected scattering.

In prediction of the back scatter signal expected from theory it has been found necessary to take account of the reflection properties of the cell windows 18, 20 and those of any other plane surfaces in the scattering region, such as protection windows, etc.

The back-scatter signals are relatively weak at all particle sizes and only become significant when the particle sizes become small and scattering becomes more isotropic. Thus as size reduces the strongly dominant forward scattering becomes weaker until it has reached the same intensity as the back-scatter.

This situation means that if forward scatter light were to be back reflected, even inefficiently (for example from a cell window), then it would significantly corrupt the back-scatter signals The mechanisms for cell reflection in the standard form of cell are as shown below in FIG. 9.

The principle illumination, or incident beam, is shown above at 84 on the main axis, propagating left to right. The main scattering components are shown from a notional single particle 86. These rays are those predicted by the use of conventional light scattering theories, such as Fraunhofer or Mie, etc.

Additional ray paths 88 exist if each plane surface of the cell 16 is considered to have finite reflectivity. These are shown above the incident beam 84 and displaced higher on the figure to aid visibility. Sing from the centre and working upwards we have, the 0° reflection of the unscattered beam 90,91 that is back-reflected and then forward scattering off the particle. The forward scattering produces two beams since there are two cell window surfaces. Then there are the two components 92, 93 caused by reflection of the forward-scattered light emerging from the cell without further scattering.

Any other plane surfaces in the system demonstrate the same basic behaviour, and therefore any further surfaces between cell and detector generate similar signals. Because the detectors have limited collection range caused by the typical apertures present in the optical system it is generally only the 0° back reflections that needs to be accounted for with these additional windows. The 0° reflected beam propagates back through the system until it again passes through the cell and any subsequent scattering is then directly in the line of sight of the detectors.

Each reflection depends upon the reflectivity of the surface involved and the angle of incidence of the beam. By the appropriate use of anti-reflection coatings it is possible to minimise reflections, particularly those effects involving 0° reflections. However for high angle of incidence reflectivity values of up to 10% can be experienced, even with optimised surfaces/coatings.

The original back-scatters light can also be forward scattered although this is usually a small effect due to the strong dominance of the forward signal. However for the smallest sizes, where light has become almost completely isotropic it is useful to take account of the reflection of the back scattered components. In the diagram above this is shown at R, and displaced downward from the diagram centre.

Reflections are cumulative since the first reflected beam might suffer further reflection before exiting the cell. However whilst reflectivities are <10% any second reflection will have reduced to a <1% effect and thus can be safely ignored. For the purposes of the models it is normally sufficient to include only first reflection behaviour for each mechanism.

The overall effect of these multi-component reflections is simple, a practical reflectivity $R_1$ and $R_2$ can be determined for the cell which describe the grossed up cell behaviour at the scattering angle concerned. Thus $R_1$ describes the effect where light originally scattered to angle θ will be reflected into the back-scatter angle 180-θ. Generally because of their different composition $R_1$ and $R_2$ are not identical, despite the apparent symmetry of the cell.

This makes clear that the back-scatter angle 180-θ is corrupted by a signal component from forward angle θ. To take account of this theoretically it is necessary to integrate the appropriate light scattering theory over the back-scatter angles, and those forward angles mirrored by the cell. These two signals can then be combined according to the reflectivity $R_1$. The need to account for the mirror angles doubles the computational load for the calculation of the scattering matrices, essential to the analysis of data to particle size.

An advantage accrues in this computation if the large angle detectors 34, 36 and back scatter detectors 38, 40 operate at angles that are mirror symmetric and are preferably identical in construction. If for example back scatter detector 40 is mirror symmetric with large angle detector 36 then the integration of reflection angles appropriate to back scatter detector 40 has already been accomplished in computing the forward scatter at large angle detector 36. Thus the necessary reflection corrections can be performed using the standard theory. For the case mentioned the correction would be $$BS_2^* = (1-R_2)(BS_2 + R_1 FS_1)$$

$BS_2$=reading at back scatter detector 40
$FS_1$=reading at large angle detector 36
Where $BS_2^*$ is the corrected scattering matrix signal under any given condition where $BS_2$ and $FS_1$ were the original theoretical predictions without reflections assumed.

Thus we compensate the detected back scatter signals by an amount dependent upon the detected forward scatter signals to take into account reflections.

The effect of accounting for cell reflections in the performance of the size analysis is extremely beneficial at all particle sizes. Without cell reflection correction the system under-predicts the amount of back-scatter light present for a given material. The excess causes the instrument to assume that sub micron particles are present too, since they can give rise to back-scatter signals whilst barely altering the forward scatter data.

By accounting for the cell reflections the system is able to correctly predict the back-scatter signal excess, thus improving accuracy of measurement for sub micron sizes.

The mirror symmetry of the large angle detectors 34, 36 and the back scatter detectors 38, 40 detectors offers a computational advantage in the calculation of scattering matrices only, it does not affect the sizing performance directly.

Although compensation for reflections from cell surfaces have their major use in back scattering we may additionally or alternatively compensate the detected signals for forward scattering using input from detected back scatter signals, but this is likely to be far less significant.

In the absence of particles in the cell 16 there is no scattering of the laser 2 beam or beam from the LED 42 and thus in theory the entire beam will pass through the hole 48 in the wafer 46 and onto the transmission detector 50. If particles are introduced to the cell 16 of the system then light is both absorbed by the particles and scattered into other angles resulting in a reduction in the signal received on the transmission detector 50. It is normal to measure the transmission before the introduction of particles $T_{RE}$ and when particles are present in the cell 16, $T_{RS}$. This is used to calculate the "obscuration" of the laser beam, which is given by:

$$O_R = 1 - T_{Rs}/T_{RE}$$

The obscuration of the laser beam $O_g$ is used both in the data processing to obtain particle size and as a diagnostic to assist in setting up a suitable particle concentration range for a particular measurement.

The scattered light from particles present in the cell 16 spreads out into all angles, having a size dependent angular intensity distribution $S(d,\theta,\phi)$. The d represents the particle size, θ the scattering angle and φ the azimuth angle. Because particles are normally in random orientation within the cell, and many thousands of particles are scattering simultaneously, the azimuthal dependence of scattering is lost. It is normal practise to sacrifice any potential size information in the φ variation to avoid the problems that would arise in needing to align particles practically within the cell. Thus these systems typically concern themselves with measurement of the θ variation, assuming φ symmetry, reducing scattering dependence to $S(d, \theta)$ Broadly, very small particles scatter light isotropically whereas large particles scatter into a very small angle around the unscattered beam. There are a number of theories available that allow complete prediction of this θ variation for a known sized particle and thus by measuring it the size of the scattering particles can be inferred.

The LED transmission detector 45 is used in an identical manner to the transmission detector 50 for the laser beam, which is to find the sample obscuration of the blue light.

$$O_B = 1 - T_{Bs}/T_{BE}$$

Using the same terminology as described earlier for the red obscuration.

Because the blue beam path is offset in the plane perpendicular to the detector plane by a relatively small amount the effect of the offset is negligible in altering the scattering angles subtended by the large angle 38, 40 and back scatter 34, 36 detectors. As a consequence these detectors can be considered as occupying identical angles of detection in measurement of the blue beam (beam from LED 42) when compared to measurement of the red beam (beam from the laser 2). Alternatively, some compensation may be applied but we do not believe it to be necessary. The detectors 34, 36, 38, 40 have gain characteristics that are different at the wavelengths emitted by the laser 2 and the LED 42. In addition the data from each detector 34, 36, 38, 40 is weighted differently in the analysis for the data obtained for the light emitted from the laser 2 and the LED 42. For these reasons the large angle 34, 36 and back scatter 38, 40 detectors have two gain calibrations recorded, one for light emitted from the laser 2 and the other for light emitted from the LED 42.

The measurement of the transmission of the light emitted from the laser 2 (and light emitted from the LED 42 in our system) is generally used in prior art systems to ensure that the particle concentration in the cell 16 is in an optimum range. The particle concentration must lie within a specified range if the signal processing is to be effective. At high concentrations it is important that multiple scattering does not occur, and if too low there is inefficient signal created on the detectors for reliable measurement. These two limits are usually expressed as an obscuration range so that the user can easily determine from the data display that both criteria are satisfactory. For example in one prior art system it is required to ensure that the obscuration signal lies in the following range:

$$0.01 < O_R < 0.5$$

In the preferred embodiment a further use has been made of these signals. Each attenuation is converted to a synthetic data point, the "Extinction". The extinction is related to transmission by the following formula $$E_B = -A. \ln(T_{Bs}/T_{Be})$$

Where $E_B$ is the extinction of the blue beam and A is an arbitrary constant.

The important property of the extinction data that is useful is that it behaves linearly with concentration whereas the original transmission and obscuration behave non-linearly. This allows the extinction to be treated as a data point and the scaling constant A can be set to scale the signal so that it fits into the data set with an appropriate significance. Thus two additional data points are derived from the transmission values and added to the data set that is analysed, the Extinction points for light emitted from the laser 42 and emitted from the LED 42.

These data points are useful in that they are sensitive to the detection of small particles. Such materials generate weak scattering signals but are effective at reducing the beam transmission, effectively generating high extinction. The combination therefore of high extinction and low scattering is indicative of fine materials. The disparity between the extinction of light emitted from the laser 2 and the LED 42 values also contains useful small size information. For larger sizes the extinction values are identical, for fine particle sizes the extinction differs. The difference increases as size reduces within a useful size range. The extinction data points therefore provide size discrimination information for small particles. They are approximately equivalent in information terms to the back-scatter detectors 38, 40.

In the preferred embodiment there are back scatter 38, 40 detectors provided and it is valid to question why the extinction points are also included, if they provide the same size information. There is a further benefit to sub-micron capability given by these points however, when the sample concentration is low the back-scatter data becomes small, poorly resolved and hence subject to substantial experimental error. The absence of extinction points would affect the ability of the preferred embodiment to repeatable measure small sizes. The transmission measurements are much easier to make and remain precise after the back-scatter signals have become unreliable.

Thus the extinction data points enhance the performance extending the size range over that obtained using the back scatter 38, 40 signals alone.

The transmission measurements of the light emitted from the laser 2 and LED 42 are made one after the other and not simultaneously. During background or sample measurements the sequence is the same. The shutter in front of the laser is turned on (passing the light from the laser 2), the blue LED 42 is switched off and measurement using light from the laser 2 is performed. When the measurement is completed (for example immediately afterwards) the shutter is introduced to block light from the laser 2 and the LED 42 is switched on. The same measurement process can then take the data obtained from the light emitted from the LED 42.

The measurement points using light emitted from the LED 42 are extracted from this second measurement and inserted into the measurement data obtained from measurements taken from light emitted from the laser 2, ending it. As the data sets are combined the respective gains of both systems are adjusted to comply with a previous system calibration. The combined data set becomes the resultant experimental data that is analysed to obtain particle size using the computational element 77 and computational device.

As particles pass through the cell 16 many thousands of particles are simultaneously illuminated and the signal received on a detector is a continuous optical summation of the scattering from all particles within the cell 16. As the particles pass through the cell 16 the sample volume population fluctuates statistically and thus the signal develops a noise like fluctuation reflecting the local population variation.

It is normal for a detector signal to be integrated over a significant time period in order to ensure that the angular intensity curve analysed is representative of a large number of particles. The integration process thus removes the statistical noise and ensures that the average is representative of the entire population of the material. This integration can be performed conventionally either by the analogue electronics, by digital electronics, by summation in a microprocessor or stand-alone computer such as a PC. In the preferred embodiment it is normally performed by a microprocessor built into the system.

In any event the detector data is produced simultaneously from all angles during any measurement from either one of the light sources 2, 42.

The parallel data produced by the system is fed to the circuitry of FIG. 8 which produces a serial stream that can be read through a common interface.

The Sample and Hold function is operated by a control signal on the common timing line 78 and effectively freezes the signal at a single time instant. By ensuring that data from all detectors is frozen at the same time before conversion it is ensured that no concentration fluctuations of the sample in the cell 16 become converted into apparent angular fluctuations by the serialisation process that follows.

At the time at which measurement is required the control signal goes from tracking to hold mode which locks the signal readings on the outputs of the sample and hold circuits. It is important that data is then converted quickly so that signal droop does not occur.

The computational device connected to the output of the ADC runs an algorithm that accesses each detector channel in sequence until all valid channels for that wavelength has been collected, digitised and held in memory. The complete data set from this single sample and hold event is called either a "sweep" or a "snap" and is the smallest unit of measurement of data.

These snaps of complete system data are then taken successively and summed by the computational element 77 to form an experiment. A snap requires a defined minimum time interval to complete, and multiple snaps are performed at the fastest rate that the computational device can accommodate. Thus the measurement time is determined by the number of snaps requested, usually controllable by the user.

Because of the time sequential nature of the measurements using light emitted by the laser 2 and the LED 42 the measurement is in fact accumulated in two sub-experiments. When the beam from the laser is incident upon the cell 16 the requested number of snaps of integration are first summed, the first experiment. Then the instrument switches automatically so that light emitted from the LED 42 is incident upon the cell 16 and performs the same number of snaps again, accumulating a new record, the second experiment. For the experiment using the LED 42 to emit the light most of the data accumulated is unused in our preferred embodiment since only the large angle 34, 36 and the back scatter 38, 40 signals are valid. These data points are extracted by the computational element 77 from the second experiment and interleaved with the first experiment extending it (extending the angular range of scattering over which reliable meaningful signals have been collected). At this point any scale compensation required between the optical components for light emitted from the laser 2 and the LED 42 is applied. Thus the computational device uses experimental results accumulated from the use of light emitted from both the laser 2 and the LED 42.

The obscuration signals for light emitted from both the laser 2 and the LED 42 from the transmission detector 50 and the LED transmission 45 detectors are also read by being passed through the multiplexer and ADC to the computational device. Similarly the signal from the laser power monitor 10 is fed through to allow the signals using the light emitted from the laser 2 to be scaled to be adjusted for any laser power variation. An obvious extension of this approach would be, as mentioned earlier, the reading of the blue monitor signal for the same purpose on blue data.

The apparatus may be provided with a visible light means situated at a top most region of the apparatus acting as a power on/off display. That is the light means may be adapted to emit light when the apparatus is in a powered on situation, and off when there is no power to the apparatus. The light means may be situated such that it is visible from substantially any angle around the machine which is advantageous in that it allows a user to readily determine whether or not there is power to the apparatus.

The light level measurements taken using light from each detector may be manipulated so that the measurements comprise a single data set as if the measurements had been taken by a single wavelength of light.

What is claimed is:

1. A particle size distribution analysis apparatus wherein there are provided a sample measurement zone for containing a sample of particles, a light emitting means for providing a source of light incident upon the measurement zone, and a detection means for measuring light levels at different scattering angles and to output signals to a computation means, enabling the size of particles contained within the sample to be determined, wherein said light emitting means comprises a first light source emitting a substantially monochromatic first wavelength of light and a second light source emitting a substantially monochromatic second, different, wavelength of light, light emitted from said second light source and the optical axis of said first light source lying in a plane which is inclined at an angle $\phi$ to a plane in which the detection means is situated, such that the scattering angles of the light emitted from said first and second light sources relative to tho detection means are substantially similar.

2. An apparatus according to claim 1 wherein said $\phi$ is substantially 90°.

3. An apparatus according to claim 1 wherein at least said first light source is a laser.

4. An apparatus according to claim 1 wherein at least said second light source is an LED (light emitting diode).

5. An apparatus according to claim 1 wherein said fist and second light sources are arranged so that beams of light emitted substantially superpose one another on said sample measurement zone.

6. An apparatus according to claim 1 wherein said second light source, in use, is pulsed.

7. An apparatus according to claim 1 wherein at least one light output stabilisation means is provided to ensure that light emitted from either of said first and second light sources is substantially constant.

8. An apparatus according to claim 7 wherein a second light source stabilisation means is provided to monitor said second light source and stabilise a light output therefrom.

9. An apparatus according to claim 7 wherein said stabilisation means comprises a primary monitoring means and primary processing means.

10. An apparatus according to claim 9 wherein said processing means is connected in a closed loop which uses the detected signal from said primary monitoring means to control an output power of said light emitted from the respective light source.

11. An apparatus according to claim 9 wherein said processing means outputs a signal representative of a light power emitted from the respective light source to enable provisions for fluctuations in the light power emitted from said light source in subsequent calculations relating to particle sizes.

12. An apparatus according to claim 1 wherein said detection means comprises the following: a large angle detector for detecting light scattered at large angles by said sample, a back scatter detector for detecting light scattered back towards the light source by said sample, forward angle detectors for detecting light scattered at medium angles by said sample and a focal plane detector for detecting light scattered at small angles by said sample.

13. An apparatus according to claim 1 wherein a computational element determines the obfuscation of the light emitted from said first light source.

14. An apparatus according to claim 1 wherein a computational element determines the obfuscation of the light emitted from said second light source.

15. An apparatus according to claim 1 wherein said detection means includes a large angle detector for detecting light scattered at large angles by said sample.

16. An apparatus according to claim 1 wherein said detection means includes a back scatter detector for detecting light scattered back towards the light source by said sample.

17. An apparatus according to claim 1 wherein said detection means includes forward angle detectors for detecting light scattered at medium angles by said sample.

18. An apparatus according to claim 1 wherein said detection means includes a focal plane detector for detecting light scattered at small angles by said sample.

19. A method of determining particle size distribution comprising illuminating a sample of particles with first and second beams of light emitted from first and second light sources respectively said beams having different wavelengths and being substantially monochromatic, said method further comprising measuring light levels around said sample to determine the particle size distribution within said sample and said method further comprising the first and second beams of light being inclined at an angle $\phi$ to a plane in which the light levels are measured.

20. A method according to claim 19 wherein said first light source is an LED.

21. A method according to claim 20 wherein said LED emits blue light.

22. A method according to claim 19 wherein said sample is illuminated with light from said first and second light sources sequentially.

23. A method according to claim 19 wherein light level measurements are manipulated so that said measurements comprise a single data set as if the measurements had been taken by a single wavelength of light.

24. A method according to claim 19 in which detected forward angle scattering signals are used to compensate detected back scattering signals for reflections of forward scattering, thereby producing a processed back scattering signal that is not the same as the detected back scattering signal.

* * * * *